Figure 1:
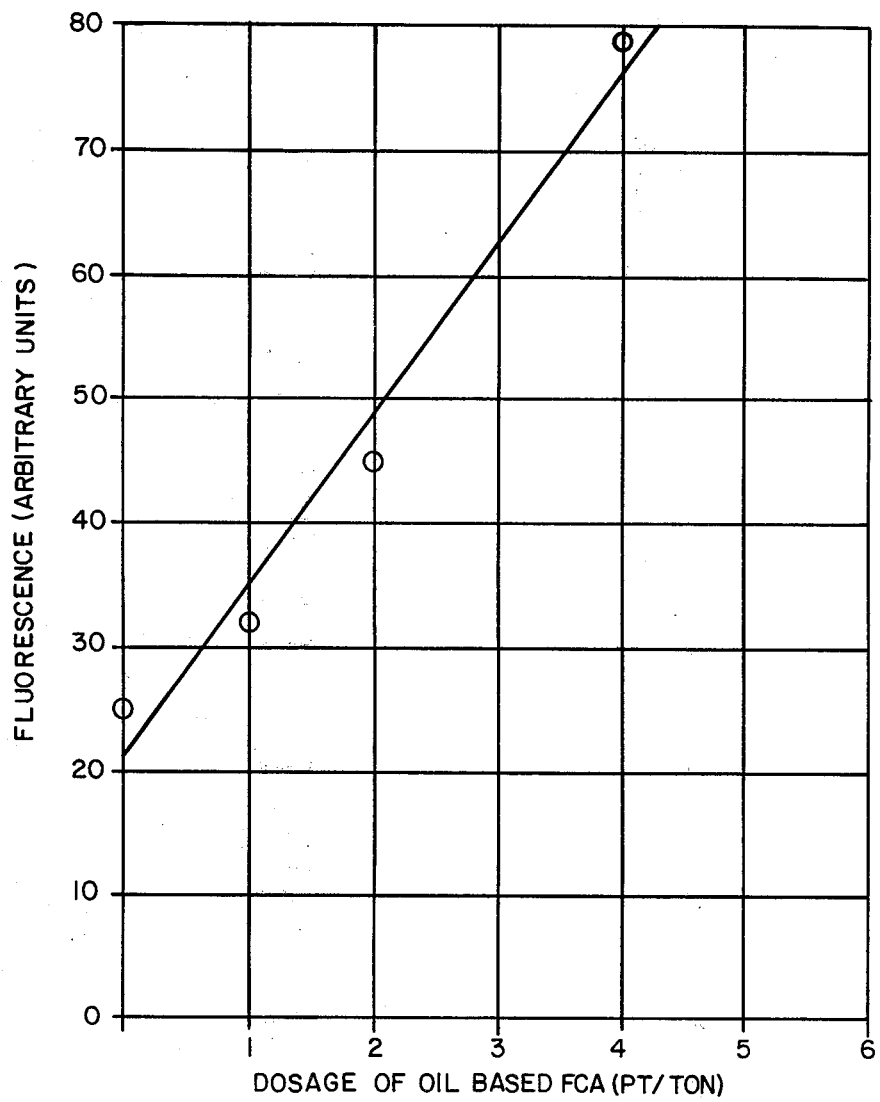

United States Patent [19]

Kugel

[11] 4,300,908

[45] Nov. 17, 1981

[54] METHOD FOR THE DETERMINATION OF DOSAGE OF FREEZE CONDITIONING AGENTS ON COAL

[75] Inventor: Roger W. Kugel, Warrenville, Ill.

[73] Assignee: Nalco Chemical Company, Oak Brook, Ill.

[21] Appl. No.: 163,022

[22] Filed: Jun. 26, 1980

[51] Int. Cl.$^3$ ............................................. G01N 21/00
[52] U.S. Cl. ..................................... 23/230 R; 116/201
[58] Field of Search ...................... 23/230 R; 44/6, 41; 116/200, 201, 206, 211; 201/41

[56] References Cited

U.S. PATENT DOCUMENTS

| | | | |
|---|---|---|---|
| Re. 17,383 | 7/1929 | Englund | 23/230 R X |
| 1,989,526 | 1/1935 | Powell | 44/6 |
| 2,207,348 | 7/1940 | Jones et al. | 23/230 EP |
| 2,992,902 | 7/1961 | Hudson | 23/230 R |
| 3,149,068 | 9/1964 | Biederman, Jr. et al. | 23/230 R X |
| 3,298,804 | 1/1967 | Schoch | 44/6 |
| 3,794,472 | 2/1974 | Macaluso et al. | 44/6 |

Primary Examiner—Arnold Turk
Attorney, Agent, or Firm—John G. Premo; Robert A. Miller

[57] ABSTRACT

A method of determining the dosage of freeze-conditioning agents applied to coal, which method comprises the following steps:
(1) treating the coal with a small amount of a freeze-conditioning agent containing a compatible fluorescent dye;
(2) extracting the treated coal with a solvent for the freeze-release agent and determining the fluorescence of such extract;
(3) extracting a similar treated coal sample to which a known amount of the freeze-conditioning agent has been further added and determining the fluorescence of this extract;
(4) setting up a proportionality between the fluorescence values of extracts (2) and (3) with the corresponding dosages of freeze-conditioning agents and solving for the unknown dosage originally applied to the coal.

2 Claims, 3 Drawing Figures

FLUORESCENCE DETECTION OF AN OIL BASED
FCA IN HEPTANE EXTRACTS OF COAL

FLUORESCENCE DETECTION OF AN OIL BASED
FCA IN HEPTANE EXTRACTS OF COAL

FLUORESCENCE DETECTION OF AN
OIL BASE FCA IN HEPTANE

DOSAGE DETERMINATION OF RHB-GLYCOL-BASED FCA
ON COAL BY THE FLUORESCENCE METHOD

METHOD FOR THE DETERMINATION OF DOSAGE OF FREEZE CONDITIONING AGENTS ON COAL

INTRODUCTION

Coal particles, especially fine particles or small lumps, are known to freeze together when the surfaces are wet and are in a water-freezing environment. This freezing is objectionable because it makes difficult the unloading or dumping of railway coal cars. It also makes difficult the movement of coal out of outdoor coal storage piles in a condition for fuel or other use.

The freezing problems of coal particles are not particularly critical in coal with lump sizes wherein the smallest dimension of the particles or lumps is in the order of about 2 inches or more. Even if such particles or lumps freeze together, they can generally be broken apart relatively easily. Coal particles such as a stoker coal and industrial screenings present freezing problems, however. Stoker coal generally has lump sizes of about 1½ to 2 inches while industrial screenings generally embrace particle sizes as low as as about 100 mesh and as high as about 1½ inches, and may include coal fines known as coal dust.

In U.S. Pat. No. 3,298,804 it has been shown that certain fatty substituted imidazolines when combined with certain hydrocarbon oils are effective in preventing coal particles from freezing together. Commercial applications of this type of treatment for coal particles has shown the products to be successful.

In addition to products of the type described in U.S. Pat. No. 3,298,804, it is now known that freeze conditioning agents may be composed of water-soluble materials such as aqueous solutions or emulsions of polyhydric alcohols such as ethylene glycol.

While these freeze conditioning agents are now used extensively to prevent freezing of the coal particles, their utilization may be enhanced and in certain cases would be more wide spread if it were possible to analyze the coal which had been treated with these freeze-conditioning agents to determine the amount that had been coated on the coal particles.

Such an analytical technique should be simple and easy to perform under field conditions. It also should be capable of being performed by relatively non-skilled technicians.

THE INVENTION

A method of determining the dosage of freeze-conditioning agents applied to coal, which method comprises the following steps:

(1) collecting a sample of coal treated with a small amount of a freeze-conditioning agent containing a compatible fluroescent dye;
(2) extracting the treated coal with a solvent for the freeze-conditioning agent and determining the fluorescence of such extract;
(3) extracting a similar treated coal sample to which a known amount of the freeze-conditioning agent has been further added and determining the fluorescence of this extract;
(4) setting up a proportionality between the fluorescence values of extracts (2) and (3) with the corresponding dosages of freeze-conditioning agents and solving for the unknown dosage originally applied to the coal.

In more general terms, a method has been developed for the analysis of coal for the dosage of freeze-conditioning agents. This method is simple and fast and may be applied in the field as well as in the laboratory. The technique involves extracting the coal with a suitable solvent, filtering, and quantitatively measuring the fluorescence from the filtrate.

In the case of the fuel oil-based freeze-conditioning agents, the characteristic blue fluorescence (350–450 nm) from the naturally occurring unsaturated compounds in the fuel oil may be detected by this method. The treated coal may be extracted with a non-polar solvent (such as, e.g., heptane or carbon tetrachloride) and the dosage of freeze-conditioning agent measured by a method of standard additions similar to that described above. Note that a fluorescent dye may also be added to a fuel oil-based product to enhance detectability. It is not unusual for such dyes to be detectable down to the parts per trillion concentration levels.

In a relatively broad aspect of the invention, the fluorescent dye is added to either type of freeze-conditioning agent, e.g. oil-based or glycol-based. This allows more accurate determination of the concentration of the agent on the coal particles.

The Fluroescent Dyes

The fluorescent dyes are those dyes that fluoresce or are luminous when exposed to ultra-violet light. A typical fluorescent dye of the water-soluble type is Rhodamine B. N-[9-(2-Carboxyphenyl)-6-(diethlamino)-3H-xanthen-3-ylidene]-N-ethylethanaminium chloride which is described as Compound 7973 in *The Merck Index*, Ninth Edition, Merck & Co., Inc., 1976. The amount of these dyes used to treat the coal release agents to provide uniformity of fluorescence is within the part per million range, e.g. 1–25 ppm with 5–10 ppm giving good results in most instances.

Other fluorescent dyes are briefly described in Kirk-Othmer's *Encyclopedia of Chemical Technology, Second Edition, Volume* 15, John Wiley & Sons, Inc., 1968, p. 456.

EXAMPLES

To illustrate the invention, the following are given by way of example:

Example 1

To demonstrate the fact that the dosage of a fluorescent material on coal is directly proportional to the fluroescence intensity of extract of the treated coal, the following experiments were carried out.

Samples of Illinois coal were treated with 0, 1, 2, and 4 pints per ton of an oil-based freeze-conditioning agent. These coal samples were extracted with heptane (100 ml solvent/100 gm coal). The fluroescence intensities of these extracts were measured relative to pure heptane using a Turner Model 111 fluorometer. The results of these measurements are shown in FIG. 1. A standard concentration fluorescence curve for solutions of this oil-based FCA in heptane is shown in FIG. 2 for comparison.

Samples of Illinois coal were treated with 0, 1, 2, 3 and 4 pints per ton of a glycol-base freeze-conditioning agent containing 10 ppm of Rhodamine B dye. These coal samples were extracted with methanol (100 ml solvent/100 gm coal). The fluorescence intensities of these extracts were measured relative to pure methanol using the Turner Model 111 fluorometer. The results of these measurements are shown in FIG. 3.

Figure 2:
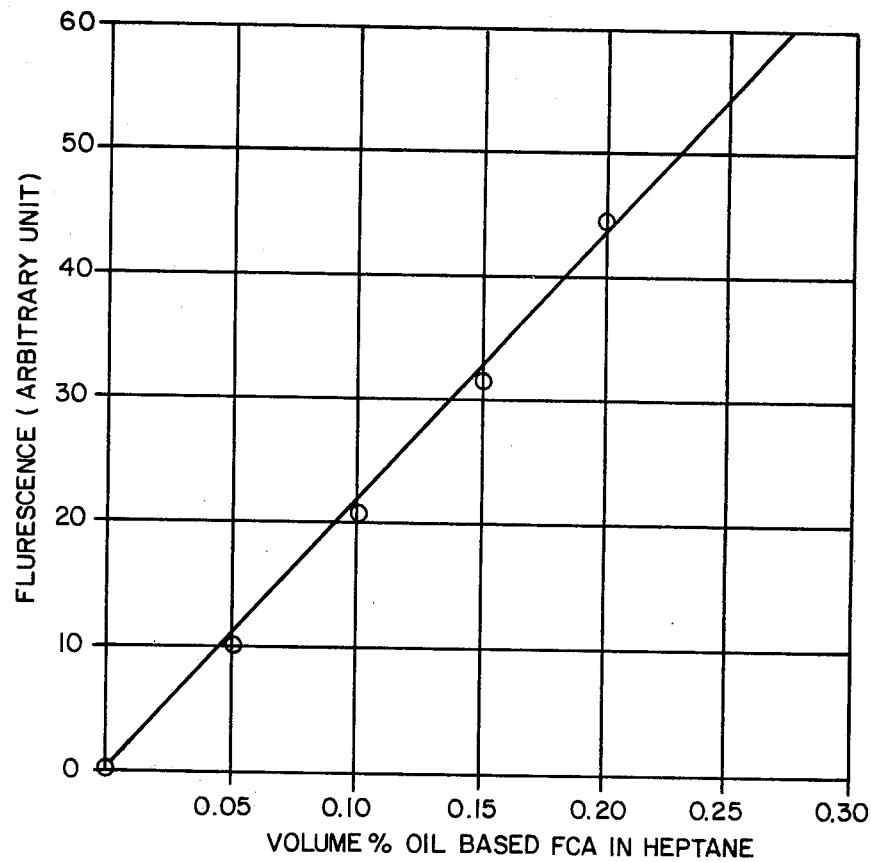
Figure 3:
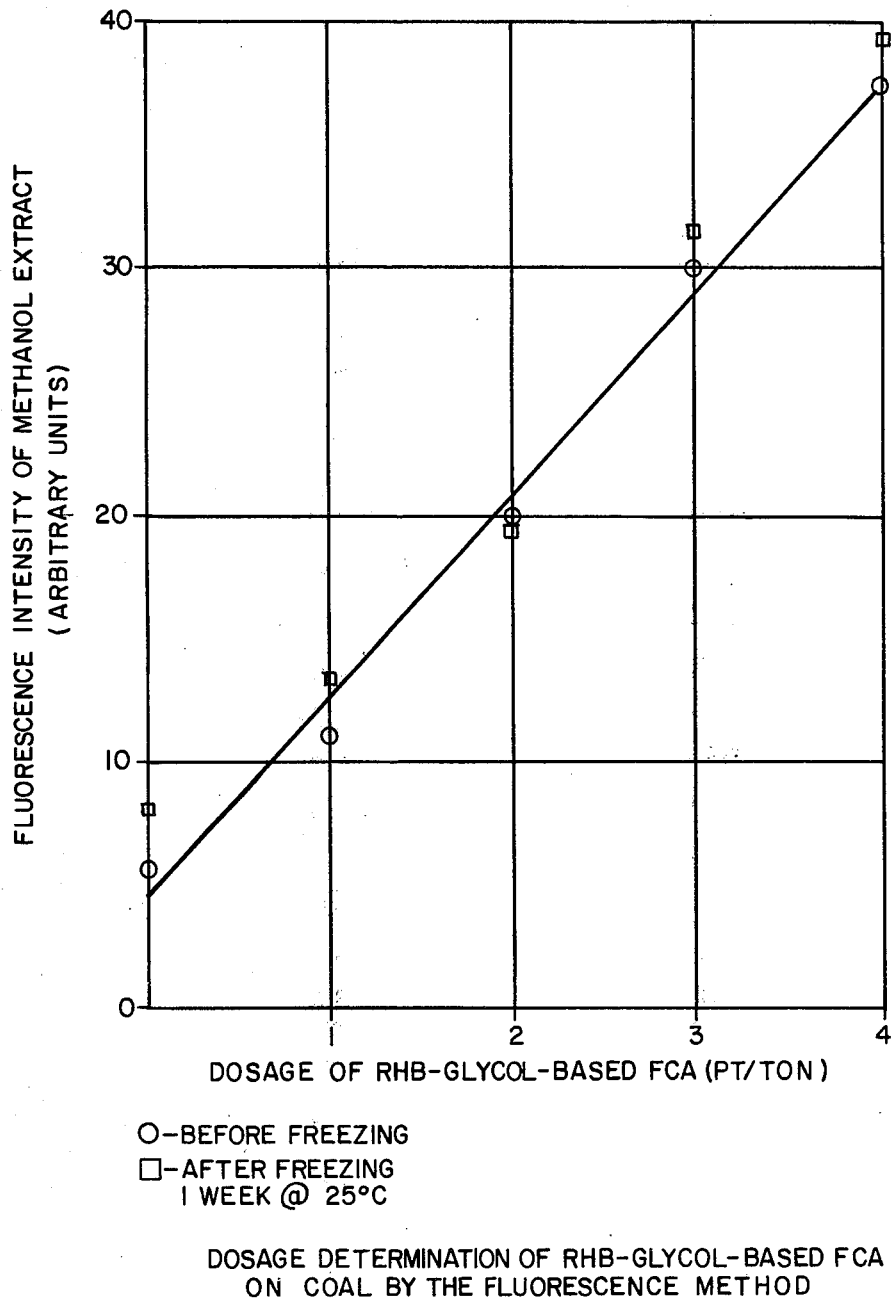

Note that the curves in FIGS. 1–3 are fairly linear indicating a direct proportionality between dosage and fluorescence intensity.

Example 2

A sample of a Kentucky coal was sprayed in the laboratory with 2.0 pints/ton of an ethylene glycol-based freeze-conditioning agent containing 10 ppm of Rhodamine B dye. The applied dosage of freeze-conditioning agent on this coal sample was measured by the fluorescence method and compared with the actual dosage of 2.0 pints/ton. Two representative 100-gram subsamples of this treated coal were weighed out in 8 oz. jars. To one of these samples was added 0.104 ml of the Rhodamine B-containing ethylene glycol-based freeze-conditioning agent. This is the equivalent of an additional 2.0 pints/ton of this agent. Both samples were extracted with 100 ml of a proprietary extraction solvent (containing methanol, ethylene glycol, and water) and filtered. The fluorescence intensities of these extracts were measured using the Turner Model 111 fluorometer. These intensities given in relative units are 45.8 for the treated sample and 90.0 for the treated plus spiked sample. If the dosage of the treated sample is x pints/ton then the dosage of the treated plus spiked sample is (x+2) pints/ton. Since the applied dosage of freeze-conditioning agent is directly proportional to the extract fluorescence intensity, the following proportionality may be used to determine the original applied dosage.

$$\frac{x}{x+2} = \frac{45.8}{90.0}$$
$$x = \frac{2(45.8)}{90.0 - 45.8}$$
$$x = 2.07 \text{ pints/ton}$$

This compares favorably with the actual dosage of 2.0 pints/ton originally applied to this coal.

Having thus described my invention, it is claimed as follows:

1. A method of determining the dosage of freeze-conditioning agents applied to coal which method comprises the following steps:
    (a) collecting a sample of coal treated with a small amount of a freeze-conditioning agent containing a compatible fluorescent dye;
    (b) extracting the treated coal with a solvent for the freeze-conditioning agent and determining the flurorescence of such extract;
    (c) extracting a similar treated coal sample to which a known amount of the freeze-conditioning agent has been further added and determining the fluorescence of this extract;
    (d) setting up a proportionality between the fluorescence values of extracts (b) and (c) with the corresponding dosages of freeze-conditioning agents and solving for the unknown dosage originally applied to the coal.

2. A method of determining the dosage of hydrocarbon, oil-containing, freeze-conditioning agents applied to coal, which method comprises the following steps:
    (a) collecting a sample of coal treated with a small amount of a freeze-conditioning agent containing a compatible fluorescent dye;
    (b) extracting the treated coal with a solvent for the freeze-conditioning agent and determining the fluorescence of such extract;
    (c) extracting a similar treated coal sample to which a known amount of the freeze-conditioning agent has been further added and determining the fluorescence of this extract;
    (d) setting up a proportionality between the fluorescence values of extracts (b) and (c) with the corresponding dosages of freeze-conditioning agents and solving for the unknown dosage originally applied to the coal.

* * * * *